US00PP16310P3

(12) United States Plant Patent
Chahbandar

(10) Patent No.: US PP16,310 P3
(45) Date of Patent: Mar. 7, 2006

(54) ARTICHOKE PLANT NAMED 'BCS 7-12'

(50) Latin Name: *Cynara scolymus*
Varietal Denomination: BCS 7-12

(76) Inventor: Medhat Chahbandar, Domaine la Quintane, Torreilles (FR), 66440

( * ) Notice: Subject to any disclaimer, the term of this patent is extended or adjusted under 35 U.S.C. 154(b) by 0 days.

(21) Appl. No.: 10/371,880

(22) Filed: Feb. 20, 2003

(65) Prior Publication Data

US 2004/0168240 P1 Aug. 26, 2004

(51) Int. Cl.
*A01H 5/00* (2006.01)

(52) U.S. Cl. ..... Plt./258
(58) Field of Classification Search ..... Plt./258
See application file for complete search history.

(56) References Cited

U.S. PATENT DOCUMENTS

PP12,206 P2 11/2001 Cofer
PP12,208 P2 11/2001 Cofer
PP14,578 P2 * 3/2004 Colfer ..... Plt./258

* cited by examiner

*Primary Examiner*—Kent L. Bell
*Assistant Examiner*—W. C. Haas
(74) *Attorney, Agent, or Firm*—Townsend and Townsend and Crew LLP

(57) ABSTRACT

A new and distinct cultivar of Artichoke plant named 'BCS 7-12'. This new variety is characterized by red or violet bud color. Further, 'BCA 7-12' has a significantly larger fruit size and an earlier maturation compared to other red artichoke varieties. This variety has also shown to be more vigorous than its parents with a larger leaf area.

4 Drawing Sheets

Botanical designation: *Cynara scolymus* L.
Variety denomination: 'BCS 7-12'.

BACKGROUND OF THE INVENTION

The present invention comprises a new and distinct cultivar of artichoke plant, botanically known as *Cynara scolymus* L., and herein referred to by the cultivar name 'BCS 7-12'. This new variety is characterized by red or violet bud color. It has a significantly larger size and matures earlier compared to other red artichoke varieties known to the inventor. This variety has also shown to be more vigorous than both parent varieties with a very large leaf area.

*Cynara scolymus* L., commonly known as Globe artichoke, is a perennial herb and is a member of the family Asteraceae, also known as the Compositae family. Globe artichokes comprise: leaves, which are pinnately lobed, but primarily spineless; globose capitula composed of overlapping layers of large involucral bracts; and receptacles, which are enlarged and fleshy. Globe artichoke plants are essentially grown for the production of the immature flower heads (or buds). The immature buds are harvested before the appearance of sexual organs (or the mature flower) and are considered vegetable delicacies. Fresh artichokes may be steamed, boiled, or baked after which the fleshy receptacle, inner and outer bracts, and parts of the floral stem may be eaten.

The new cultivar is a product of a planned breeding program carried out by the inventor near Perpignan, France. It originated as a single plant, which was selected from a hybrid cross of the artichoke variety 'Chrysantheme' (unpatented, the pollen parent); and the artichoke variety 'BH 35-22' (unpatented, the seed parent). The inventor performed asexual reproduction on a single plant of the new cultivar via division. It was demonstrated that the combination of characteristics as herein disclosed for the new cultivar are firmly fixed and retained through successive generations of asexual reproduction.

BRIEF SUMMARY OF THE INVENTION

The following traits have been repeatedly observed and are determined to be basic characteristics of 'BCS 7-12'. These traits in combination distinguish the artichoke variety as a new and distinct cultivar. 'BCS 7-12' is characterized by a red or violet fruit bud color. It has a significantly larger size (weight can be as much as 600–650 gm.) and matures earlier compared to other red artichoke varieties known to the inventor. 'BCS 7-12' has also proven to be more vigorous than its parents with a larger leaf area.

'BCS 7-12' has not been observed under all possible environmental conditions. The phenotype of the new cultivar may vary with variations in environment such as temperature, humidity, light intensity and day length, without any change in the genotype. The following observations, measurements and values describe the new cultivar as grown in Lompoc, Calif. under conditions that closely approximate those generally used in horticultural practice.

Lompoc is located on California's central coast in Santa Barbara County. Conditions can vary in the summer months. Air temperatures can range between the low 60's to 80's. The relative humidity is generally high. Prevailing winds are northwesterly and rainfall averages 12 inches per year.

In the following description, holding quality was measured by the physical appearance of the head. This includes the head's appearance following 3 and 7 day storage periods in cold storage at 34° F. The head's exterior (oxidation) was observed at each of the two observation points. Browning and blackening of plant tissue was evaluated as light, moderate and extreme. Overall storage response was measured by observing heads following 3 and 7 day cold storage periods. These observations concentrated on visible color variability and/or presence of lesions or other cosmetic anomalies. Leaf ratio (L/W) was determined by dividing representative leaf sample lengths by their width. Finally, head response (weather) was determined by observing the heads at maturity. These field observations focus on the presence or absence of bronzing, necrotic or chlorotic lesions or any abiotic responses to environmental conditions.

BRIEF DESCRIPTION OF THE DRAWINGS

This new variety is illustrated by the accompanying photographic drawings. The colors in the photographs are as true to those of the plant as can be reasonably obtained from conventional photographic procedures.

DETAILED DESCRIPTION

Figure 1:
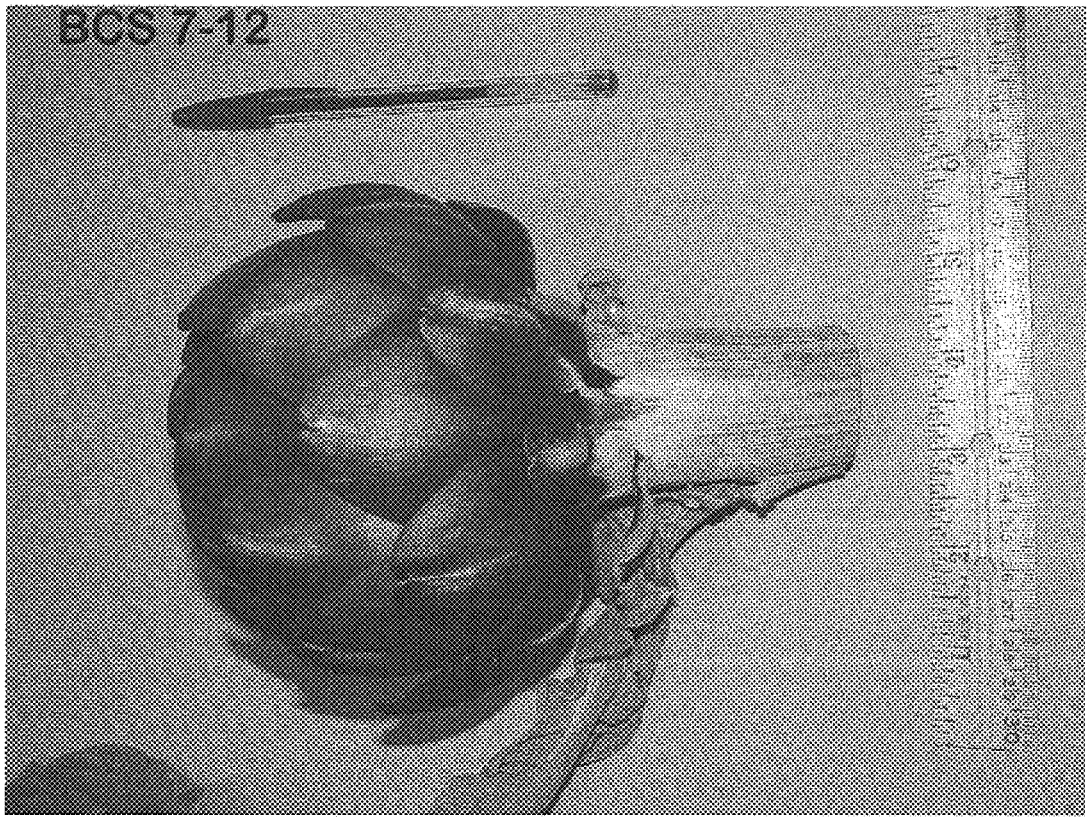
FIG. 1 shows a side elevational view of 'BCS 7-12's' fruit in full color.
Figure 2:
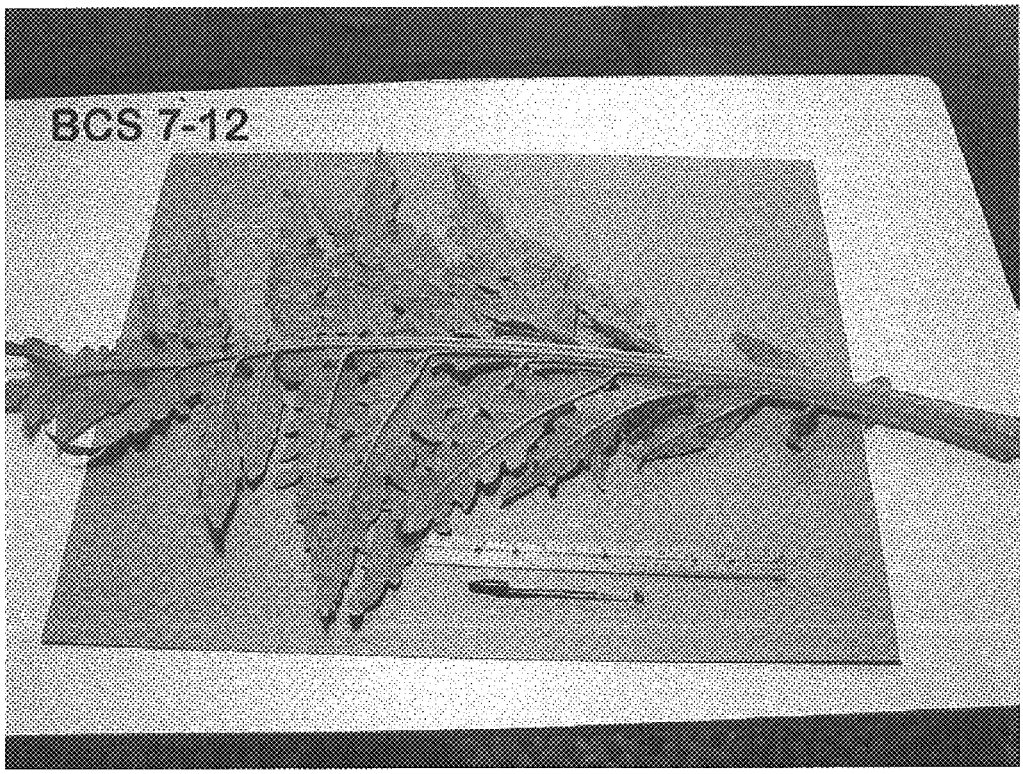
FIG. 2 shows a side elevational view of 'BCS 7-12's' foliage in full color.
Figure 3:
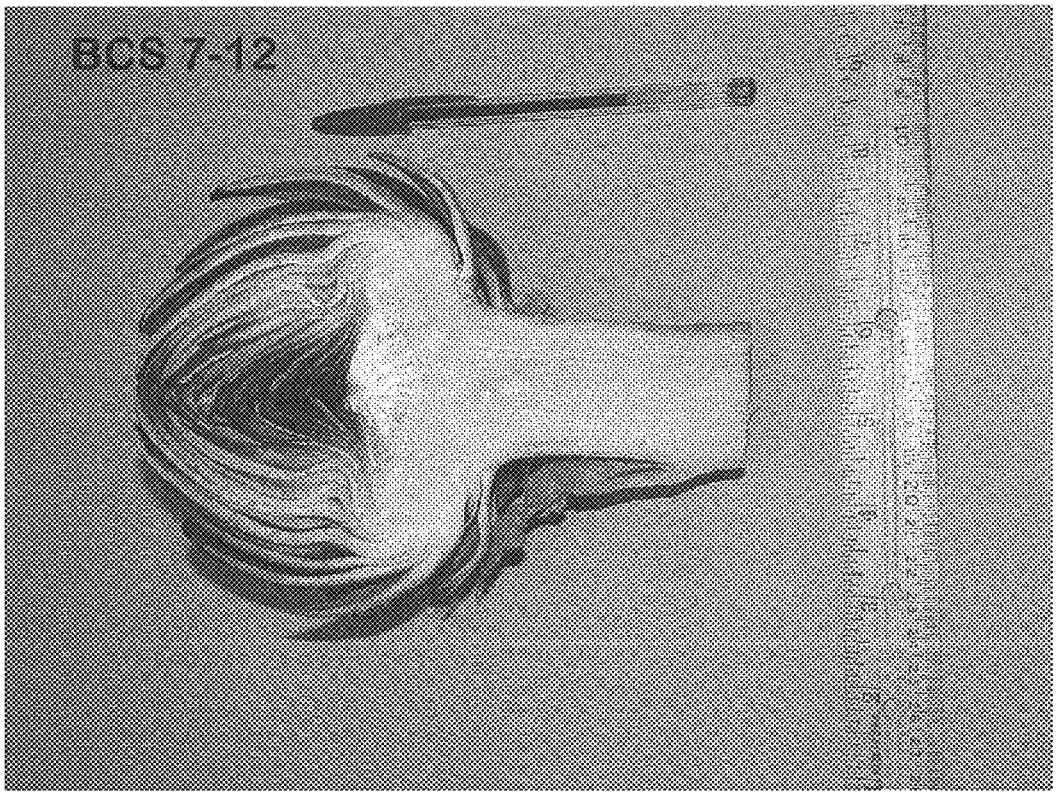
FIG. 3 shows a close-up view of the vertical cross-section of 'BCS 7-12's' fruit in full color.
Figure 4:
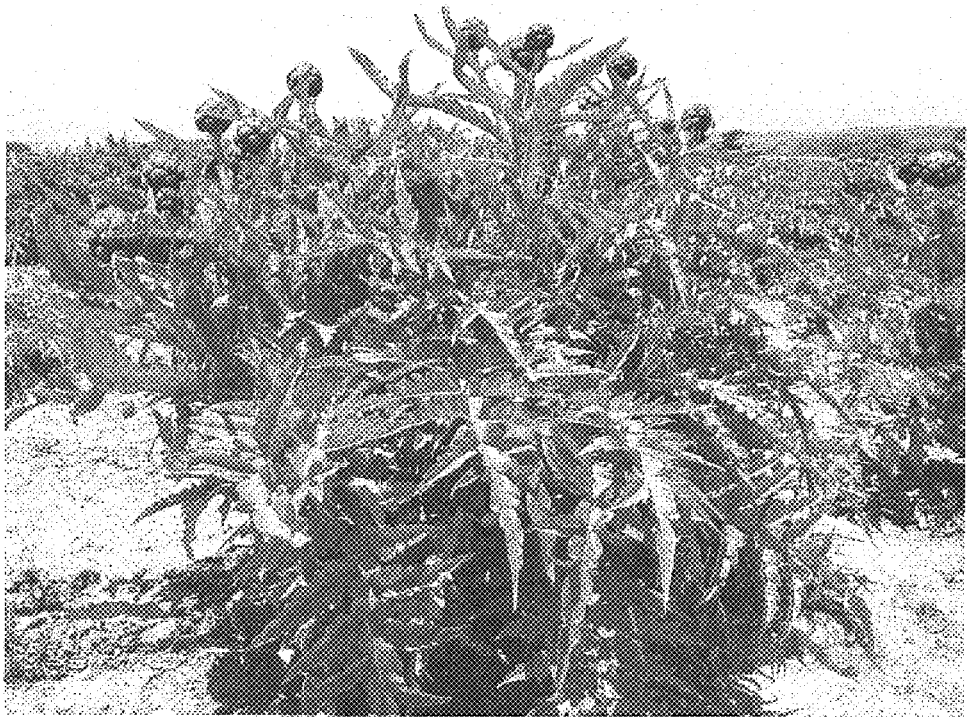
FIG. 4 shows a side elevational view of the 'BCS 7-12' plant in whole.

The following observations, measurements, and values describing the new artichoke plant are based upon observations of plants grown in Lompoc, Calif. The parent cultivars listed above are, to the inventor's knowledge, the closest prior art to the claimed plant variety. The variety was selected as a single plant that was then reproduced. Selection was performed in an outdoor field setting. Unless otherwise indicated, the data were collected from plants that originated from asexually reproduced plants that had been grown in Perpignan by micropropagation in vitro using meristem culture, acclimatized in California, and then vegetatively divided. The plants were grown in the soil in rows where row spacing (bed centers) was at 80 inches, and individual plant spacing at 36 inches. Unless otherwise indicated, the measurements described herein were obtained from plants grown in accordance with the following: after acclimatization, plants were planted in the field in July 2001 and harvested in March of 2002. The plants were cut back and split. New plants were planted in July of 2002 and measurements performed in December of 2002 or January of 2003. Color references are measured against The Royal Horticultural Society Colour Chart.

Plant growth is indicated below as "vigorous". Exemplary growth data showed that plants planted from tissue culture on Jun. 9, 2004 grew to an average of 50.5 inches in height and 100 inches in width by Jan. 26, 2005; and plants planted from tissue culture on Jul. 21, 2004 grew to an average of 48 inches in height and 91 inches in width by Jan. 26, 2005.

General:

*Parentage*.—Hybrid cross between 'Chrysantheme' (pollen parent) and 'BH 35-22' (seed parent).

*Classification*.—*Cynara Scolymus* L.

*Propagation*.—Asexual production by division.

Plant:

*Height*.—83.9 to 111.8 cm; average 100.1 cm.

*Width*.—177.8 to 236.2 cm; average 205.2 cm.

*Form*.—Full.

*Growth habit*.—Upright.

*Vigor*.—Vigorous.

Main stem:

*Main stem length*.—Approximately 116.8 to 138.4 cm.

*Main stem width* (*w/leaves*).—Approximately 62.2 to 73.7 cm.

*Main stem diameter*.—7.0 to 9.2, average 8.0 cm.

*Average internode distance*.—Approximately 7.4 to 8.9 cm.

Side shoots:

*Length*.—12 to 44 cm; mean 32 cm.

*Diameter*.—2 to 2.7 cm; mean 2.3 cm.

*No. of leaves per shoot*.—2 to 4 leaves.

*Average internode distance*.—5.5 to 7 cm.

*Average number*.—7.2 per plant.

*Development*.—Vigorous.

*Color*.—Green group between 143B and 143C.

*Foliage density*.—Dense; many large leaves off main stem with leafy side shoots development as well.

Capitulum:

*Primary size*.—Approximately 12.4 cm.

*Shape*.—Round, compact with slightly pyramidal.

*Texture*.—Hard and smooth.

*Fragrance*.—Tangy with citrus overtones.

Bract:

*Length*.—Approximately 7 cm.

*Width*.—Approximately 4 cm.

*Shape*.—Ovate, longer than broad, and thick.

*Texture*.—Hard and smooth.

*Number*.—Approximately 152 per head.

*Color* (*inner*).—Green group between 138A and 138B, and Greyed purple group between 183C and 183D at the tip.

*Color* (*outer*).—Greyed purple group between 183A and 183B.

*Firmness*.—Firm and fleshy with thick basal thickness.

*Spinosity*.—None, or minimal — less than 1 mm.

*Basal thickness*.—6 to 17 mm.

Miscellaneous:

*Heart description*.—Slightly concave; and full, more flat than 'Green Globe' (unpatented), well developed with thick bract connection.

*Heart color*.—Yellow green group 145D.

*Receptacle thickness*.—1.7 cm.

*Florets*.—Sterile.

*Pappus length*.—1.8 cm.

*Pappus color*.—Yellow green group 145D.

*Head firmness*.—Firm, heads are dense and solid.

*Gloss*.—High; more glossy than 'Green Globe'.

*Cold storage response*.—Some minor cut stem discoloration. After 7 days there is some fading of red/purple color.

*Head response* (*weather*).—After frosts the outer epidermal layer of the outer bract can separate, thus exposing a green layer underneath. Further, after prolonged exposure to sunlight the purple color becomes slightly greenish.

*Disease*.—Older leaves are susceptible to *Ramularia* leaf spot.

*Bud burst*.—March 10 to March 30.

Foliage:

*Leaf shape*.—Long, narrow, slightly oval overall, with multiple lobes such that the outer edges appear coarsely serrated, wherein the apex is acute and the petiole attaches to the center of a slightly obcordate base.

*No. of leaves on main stem.*—9 to 18 leaves.
*Leaf ratio.*—Approximately 1.8 to 2.1 cm.
*Leaf areas.*—Approximately 3,038 to 4,014 cm sq.
*Upper leaf surface color.*—Green group between 136A and 136B.
*Lower leaf surface color.*—Green group between 139B and 139C.
*Texture.*—Slight but uniformly textured; glossy with rough intervenal texture.
*Pubescence.*—Sparse, some visible pubescence on lower leaf surface.
*Lobe width.*—Approximately 11.4 to 14.9 cm.
*Lobe indentation.*—Approximately 7.0 to 7.6 cm.
*Petiole width France.*—Approximately 6.0 cm.
*Petiole width.*—Approximately 3.8 to 5.8 cm.
*Petiole thickness.*—Approximately 2.2 to 2.5 cm.
*Petiole color.*—Green group 139C.
*Petiole texture.*—Spindled, wherein multiple ridges, running parallel to the lengthwise orientation, radiate around the petiole.

What is claimed is:

1. The new and distinct variety of artichoke plant substantially as shown and described herein.

* * * * *